United States Patent [19]
Schön et al.

[11] Patent Number: 5,344,954
[45] Date of Patent: Sep. 6, 1994

[54] PROCESS FOR THE PREPARATION OF DIARYL CARBONATES

[75] Inventors: Norbert Schön; Hans-Josef Buysch, both of Krefeld; Paul Wagner, Düsseldorf; Reinhard Langer, Krefeld, all of Fed. Rep. of Germany

[73] Assignee: Bayer Aktiengesellschaft, Leverkusen, Fed. Rep. of Germany

[21] Appl. No.: 103,936

[22] Filed: Aug. 6, 1993

[30] Foreign Application Priority Data

Aug. 13, 1992 [DE] Fed. Rep. of Germany ....... 4226756

[51] Int. Cl.$^5$ .............................................. C07C 69/96
[52] U.S. Cl. .................................... 558/274; 558/270; 203/38
[58] Field of Search ................... 558/274, 270; 203/38

[56] References Cited

U.S. PATENT DOCUMENTS

| | | | |
|---|---|---|---|
| 4,410,464 | 10/1983 | Hallgren | 558/274 X |
| 4,554,110 | 11/1985 | Mark | 558/274 X |
| 5,210,268 | 5/1993 | Fukuoka et al. | 558/270 |

FOREIGN PATENT DOCUMENTS

| | | |
|---|---|---|
| 0000879 | 3/1979 | European Pat. Off. . |
| 0461274 | 12/1991 | European Pat. Off. . |
| 3308921 | 9/1983 | Fed. Rep. of Germany . |
| 3445552 | 7/1985 | Fed. Rep. of Germany . |

*Primary Examiner*—Robert W. Ramsuer
*Assistant Examiner*—Michael G. Ambrose
*Attorney, Agent, or Firm*—Sprung, Horn, Kramer & Woods

[57] ABSTRACT

Diaryl carbonates are prepared from dialkyl carbonates and phenolic compounds by transesterification in the presence of a transesterification catalyst at 60°–320° C. in an apparatus composed of two columns in a continuous procedure. In the first column, the starting materials form essentially the associated alkyl aryl carbonate, from which, in the second column, the diaryl carbonate is produced by further transesterification and disproportionation.

20 Claims, 2 Drawing Sheets

PROCESS FOR THE PREPARATION OF DIARYL CARBONATES

BACKGROUND OF THE INVENTION

1. Field of the Invention

The invention relates to a continuous process for the preparation of diaryl carbonates or alkyl aryl carbonates from dialkyl carbonates and phenols, using conventional transesterification catalysts, which is characterised in that the starting products are first reacted together in the liquid phase in counter-current and the reaction is brought to completion in a reaction column.

The preparation of aromatic and aliphatic-aromatic esters of carbonic acid (carbonates) by transesterification, starting from aliphatic esters of carbonic acid and phenols, is known in principle. This is an equilibrium reaction, the position of the equilibrium being almost completely displaced in the direction of the aliphatically substituted carbonates. Therefore, it is relatively easy to prepare aliphatic carbonates from aromatic carbonates and alcohols. However, in order to carry out the reaction in reverse in the direction of aromatic carbonates, it is necessary to displace the highly unfavourably situated equilibrium, where not only do highly active catalysts have to be used, but also an expedient procedure has to be used.

2. Description of the Related Art

For the transesterification of aliphatic carbonic acid esters with phenols, a multiplicity of effective catalysts have been recommended, such as for example alkali metal hydroxides, Lewis acid catalysts selected from the group comprising the metal halides (DE-OS (German Published Specification) 25 28 412 and DE-OS (German Published Specification) 25 52 907), organotin compounds (EP 879, EP 880, DE-OS (German Published Specification) 34 45 552, EP 338 760), lead compounds (JP-57/176 932), and Lewis acid/protonic acid catalysts (DE-OS (German Published Specification) 34 45 553). In the known processes, the transesterification is carried out in a batchwise-operated reactor at atmospheric pressure or at superatmospheric pressure, with or without an additional separation column. In this case, even with the most active catalysts, reactions times of many hours are required until even only moderate conversions of approximately 50% of phenol are achieved. Thus in the batchwise-operated transesterification of phenol with diethyl carbonate at 180° C. using various organotin compounds, as are described in DE-OS (German Published Specification) 34 45 552, yields of diphenyl carbonate in an order of magnitude above 20% are only achieved after a reaction time of approximately 24 hours; in the batchwise-operated transesterification of phenol and dimethyl carbonate with the aid of organotin catalysts as are described in EP-879, the phenol conversion is 34% of the theoretical value after 30 hours.

This means that because of the unfavourable thermodynamic conditions, the described transesterification reactions in tanks or pressurized autoclaves, even when highly active catalyst systems are used, can only be carried out highly disadvantageously in the sense of an industrial process, since very poor space-time yields and high residence times at high reaction temperatures are required, where because of the incomplete transesterification, a high distillation effort must additionally be applied which requires further energy.

Such procedures are also particularly disadvantageous since even using highly selective transesterification catalysts, at the high temperatures and long residence times of many hours, a noticeable portion of side-reactions occurs, for example ether formation and elimination of carbon dioxide.

It has therefore been attempted to displace the reaction equilibrium in the direction of the desired products by adsorption of the alcohol produced during the transesterification on molecular sieves as rapidly as possible (DE-OS (German Published Specification) 33 08 921). From the description of this reaction it is evident that a large amount of molecular sieve is required for the adsorption of the reaction alcohol, which greatly exceeds the amount of alcohol being liberated. In addition, the molecular sieves used must be regenerated after just a short time and the rate of conversion to the alkyl aryl carbonate intermediates is relatively low. Even this process, therefore, does not seem to be advantageously usable industrially.

It is known to carry out equilibrium reactions, in particular esterifications and transesterifications, in columns and to displace them in this manner advantageously in the direction of product formation (e.g. U. Block, Chem.-Ing.-Techn. 49, 151 (1977); DE-OS (German Published Specification) 3 809 417; B. Schleper, B. Gutsche, J. Wnuck and L. Jeromin, Chem.-Ing.-Techn. 62, 226 (1990); Ullmanns Encyclopädie der techn. Chemie, [Encyclopedia of Industrial Chemistry], 4th edition, volume 3, pp. 375 ff., 1973; ibid. 5th edition, volume B 4, pp. 321, 1992).

In EP 0 461 274 (WO 91/09832), a continuous transesterification process is described for the preparation of aromatic carbonates in one or more multi-stage columns connected one after the other, dialkyl carbonates or alkyl aryl carbonates being reacted with phenols and the readily volatile products, that is reaction alcohols and dialkyl carbonates being withdrawn at the head of the columns and the high-boiling products, that is aryl carbonates, being withdrawn at the foot of the columns.

An already-known process principle, carrying out transesterification reactions in columns, is thus being applied here to a specific problem, that is to the transesterification of alkyl carbonates to give aryl carbonates. However, particular engineering measures which permit the transesterification reaction to be carried out more advantageously, matching the apparatuses and procedures to the abovedescribed special problems of this difficult transesterification, are not given. Thus, for example, the manner of metering the two starting materials alkyl carbonate and aromatic hydroxyl compound is not clearly defined and neither is any advantageous technique emphasized. In a technique according to FIG. 1 of EP 0 461 274, for example, mixtures of these two starting materials are fed into the upper part of the column, the low-boiling reaction products, that is alcohols and unreacted dialkyl carbonate, are withdrawn at the head of the column and the high-boiling reaction products alkyl aryl carbonates and diaryl carbonates are withdrawn, together with unreacted dialkyl carbonates and aromatic hydroxyl compounds, at the foot of the column. In the technique according to Diagram 2 of EP 0 461 274, mixtures of alkyl carbonates and aromatic hydroxyl compounds are supplied at two different points of the column, that is at the upper and lower third of the column and starting materials/product mixtures are withdrawn as in the technique according to FIG. 1. Neither in the text nor in the examples is a clear differentiation made between conducting the starting materials in co-current and counter-current, although they can have a great influence on the result of the process.

Furthermore, the influence of temperature, pressure, catalyst concentration and liquid residence time is not considered, but only very broad ranges are quoted, even in the preferred variants, for example temperature ranges of 100° to 280° C., pressure ranges from 0.1 to 200 bar, catalyst concentrations from 0.001 to 50% by weight and liquid residence times of 0.05 to 2 hours are quoted.

Different procedures to be preferred in each case for the individual reactions occurring in the conversion of dialkyl carbonates to give diaryl carbonates, for example the first transesterification stage from dialkyl carbonates with aromatic hydroxyl compounds to give alkyl aryl carbonates according to Equation 1, the second transesterification stage to give diaryl carbonates according to Equation 2 and the disproportionation according to Equation 3, are not considered in EP 0 461 274.

(1)

(2)

(3)

(Alk=alkyl; Ar=aryl)

The embodiments of this EP 0 461 274 lead those skilled in the art to the conclusion that although the transesterification of phenols with dialkyl carbonates can be carried out continuously in a known manner by known processes in columns, it is immaterial by which variant, whether at high or low temperature, in co- or counter-current, at low or high pressure, at large or small molar ratios etc. In brief, one must conclude therefrom that in the case of this particular transesterification problem, there are no possibilities for improvement and for a more advantageous procedure. Thus just the examples quoted can be used to evaluate the actual value of this European Patent Application.

From these examples it can be seen that in the transesterification of dialkyl carbonates with phenols, even at relatively high temperatures, at elevated pressure and even at molar excesses of dialkyl carbonate of more than 3, only low conversions in the range from 10 to 15% (in the best case approximately 19%) and, especially, only very low space-time yields up to 0.02 $kgl^{-1}h^{-1}$ are achieved. This is surprising, especially since very large columns have been used, among them even a 20-plate column 6 m in length and approximately 300 l in volume. The higher phenol conversion achievable by dialkyl carbonate excesses must in any case be gained, for stoichiometric reasons, by lower dialkyl carbonate conversions. This means that the dialkyl carbonate withdrawn at the head contains only very low amounts of alcohol and thus, in an industrial process, considerably more unreacted starting product must be circulated and separated off from the small amounts of reaction alcohol. The low space-time yields, for a given production amount per unit of time, would make very large reactors and very large distillation capacities necessary.

Although the disproportionation reaction of alkyl aryl carbonates performed in accordance with the description of EP 0 461 274 in a downstream second column in accordance with Equation 3 does proceed with higher yields, for an industrial synthesis of diaryl carbonates, such a disproportionation of alkyl aryl carbonates, in comparison with the further transesterification with phenols, should be seen as less advantageous, since only every second alkyl aryl carbonate molecule is converted into the diaryl carbonate end product and the other half is returned to the starting dialkyl carbonate.

From Examples 22 to 30 of EP 0 461 274, in which reactions are described in two columns connected one after the other and the composition of the head product from the second column is mentioned as feed stream No. 6 in Diagram 4 or 5, it is clear, that in spite of the presence of considerable amounts of phenols, no alcohol is formed in the second reaction stage and accordingly the proportion of the second transesterification stage according to Equation 2 is not given or is insignificant.

In an industrial process for the preparation of diaryl carbonates, especially of diphenyl carbonate from dimethyl carbonate and phenol, not only the phenol conversion is of importance, but also the dimethyl carbonate amount which is necessary to achieve a certain phenol conversion, and the dimethyl carbonate conversion resulting from this. In practice, only low dimethyl carbonate conversions and thus low methanol concentrations in the dimethyl carbonate at the column head will be able to be achieved, for example those of 5 to 10% by weight of methanol. However, in EP 0 461 274, pure dimethyl carbonate or diethyl carbonate is used without restrictions as starting material. From the view, point of the low conversions obtained of dialkyl carbonates of only a few percent, this is understandable and certainly absolutely necessary, since because of the unfavourable equilibrium position, if alcohol-containing dialkyl carbonates were used, the conversion rates would be still lower and thus industrially unacceptable. However, methanol forms with dimethyl carbonate an azeotrope of the composition 70% by weight of methanol and 30% by weight of dimethyl carbonate, which can be separated only with great distillation effort.

However, the removal of very small amounts of the reaction methanol from the dimethyl carbonate product stream requires a particularly high separation effort, as a result of which the return of the unreacted dimethyl carbonate into the transesterification process in pure form can only be achieved with very great effort. This is also of particular economic importance, since because of the only small dimethyl carbonate conversion rates which can be achieved during a reactor pass, the circulated amounts of dimethyl carbonate are very large.

The aim of an improved transesterification process for the preparation of diaryl carbonates from dialkyl carbonates and phenols would therefore have to be, firstly to make significant amounts of alcohols tolerable in the dialkyl carbonate starting material stream and, secondly, to promote the transesterification stage according to Equation 2, that is the transesterification of phenol with alkyl aryl carbonates to give diaryl carbonate and to repress the disproportionation of alkyl aryl carbonate.

It can be deduced from the mass action law that even small amounts of alcohols would react with the already-formed aryl carbonates, because of the highly unfavourably situated transesterification equilibrium, again in the direction of the starting materials. It therefore seems pointless to realise the abovementioned first aim. The authors of EP 0 461 274 have apparently also assumed this.

The transesterification of an alkyl aryl carbonate with phenol to give diaryl carbonate according to Equation 2 is, according to the results of EP 0 461 274, apparently disadvantaged in comparison with the disproportionation of two alkyl aryl carbonate molecules according to Equation 3, or even completely repressed. It thus appeared to be highly questionable whether the second aim can be achieved. For an industrial synthesis, moreover, an increase of the space-time yields above those mentioned in EP 0 461 274 should be attempted as a third aim in order to decrease the size of the apparatuses. For this as well, EP 0 461 274 offers no solution.

SUMMARY OF THE INVENTION

Figure 1:
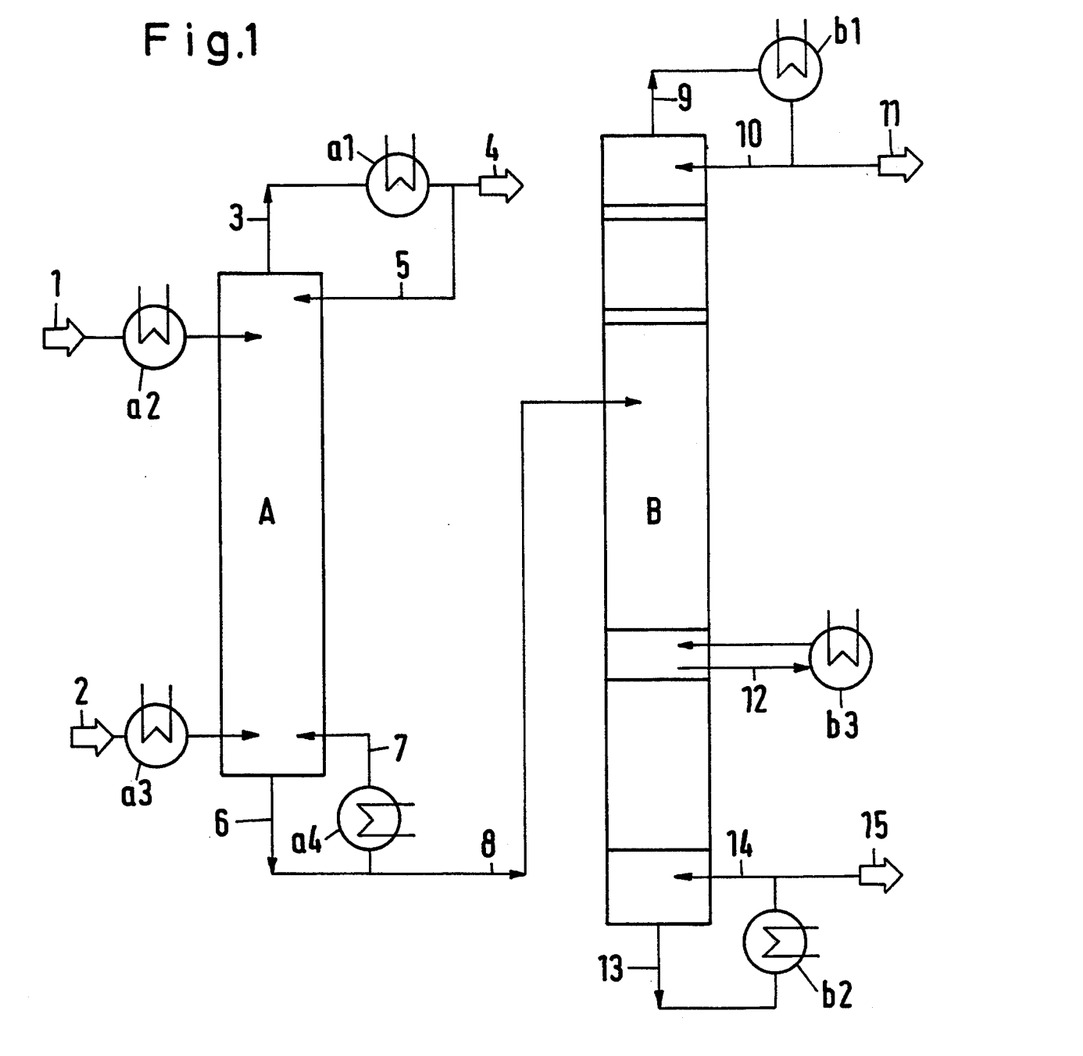
FIG. 1 and FIG. 2 show combinations of a first column A with a second column B to carry out the inventive process, whereby A is run with the feeds in countercurrent flow and B is run to complete the transesterification and to distillatively remove a dialkyl carbonate/alcohol mixture at the top of B and the diaryl carbonate at the bottom of B.
Figure 2:
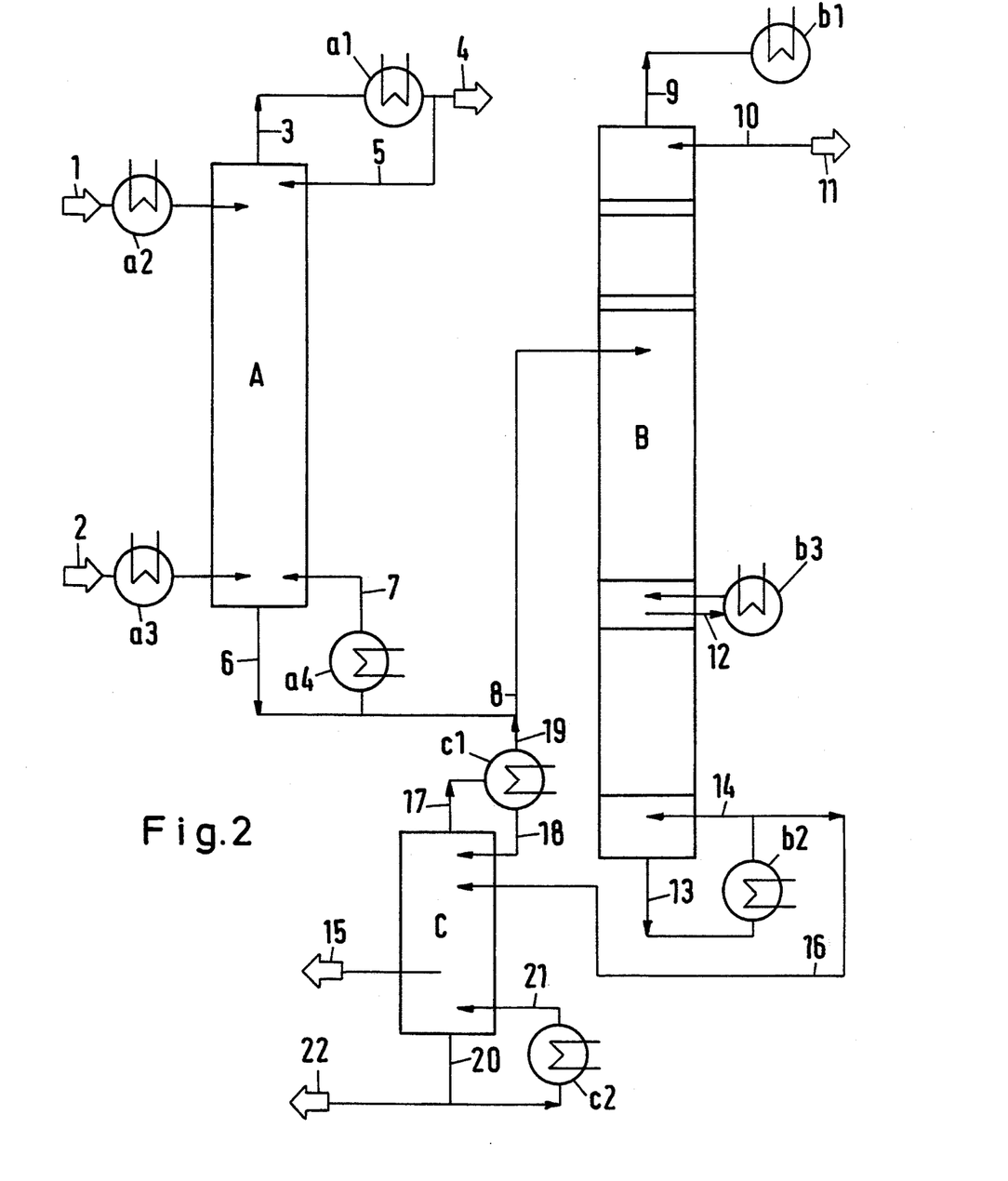

Surprisingly, it has now been found that the reaction of phenols with dialkyl carbonates to give diaryl carbonates is achievable with the targeted improvements in a two-stage process. In this case, dialkyl carbonates, which can possibly also contain significant amounts of the corresponding alcohol, are initially reacted with phenols in the sense of a "counter-current transesterification" (reactor A) and the resulting product mixture is reacted in a second column-type reactor in the sense of a "reaction distillation" (reactor B) (FIGS. 1–2 ).

A process has been found for the preparation of diaryl carbonates of the formula $$AR^1-O-CO-O-Ar^1 \qquad (I),$$

in which

Ar$^1$ denotes unsubstituted phenyl or naphthyl or mono-substituted to trisubstituted phenyl, the substituents being identical or different and belonging to the group comprising C$_1$–C$_4$-alkyl, C$_1$–C$_4$-alkoxy and halogen, by transesterification of 1 mol of aromatic hydroxyl compounds of the formula $$Ar^1-OH \qquad (II),$$

in which Ar$^1$ has the meaning mentioned,
with 0.1 to 10 mol, preferably 0.2 to 5 mol, particularly preferably 0.5 to 3 mol, of dialkyl carbonates of the formula $$R^1-O-CO-O-R^1 \qquad (III),$$

in which

R$^1$ denotes straight-chain or branched C$_1$–C$_6$-alkyl, cyclopentyl or cyclohexyl, in the presence of transesterification catalysts known per se in column apparatuses known for transesterifications, which is characterised in that the transesterification reaction is carried out in two columns connected one after the other in such a way that a) in the first column, the aromatic hydroxyl compound is conducted in the liquid state from head to bottom and the dialkyl carbonate is conducted in the gaseous state against this liquid stream, the temperature being kept in the range from 100° to 300° C., preferably 120° to 250° C., particularly preferably 150° to 240° C. and the pressure being kept in the range from 0.5 to 20 bar, preferably 0.8 to 15 bar, particularly preferably 0.9 to 10 bar, and the dialkyl carbonate containing a portion from 0 to 5% by weight, preferably 0.1 to 3% by weight, particularly preferably 0.2 to 2% by weight, of the underlying alcohol, based on the overall weight of dialkyl carbonate and alcohol, that b) at the head of the first column, the alcohol underlying the dialkyl carbonate and liberated in the transesterification is withdrawn in the gaseous state and at the bottom of the first column, a partly reacted transesterification product essentially composed of alkyl aryl carbonate is withdrawn in the liquid state, that c) the bottom stream of the first column is fed into the central part of a second column, the temperature of which is kept in the range from 60° to 320° C., preferably 65° to 305° C., particularly preferably 65° to 250° C. and the pressure of which is kept in the range from 0.05 to 10 bar, preferably 0.1 to 5 bar and particularly preferably 0.2 to 2 bar, depending on the boiling point of the bottom stream fed in from the first column, a temperature gradient being applied to this second column in such a way that the alkyl aryl carbonate contained in tile bottom stream fed in can escape from the central part of the second column essentially neither to the head nor to the bottom and that d) at the head of the second column, a mixture of dialkyl carbonate, the underlying alcohol and excess aromatic hydroxyl compound and at the bottom of the second column, diaryl carbonate, which can contain alkyl aryl carbonate and aromatic hydroxyl compound, are withdrawn.

DETAILED DESCRIPTION OF THE INVENTION

In the formation of the diaryl carbonate, the transesterification from the aliphatic to the aromatic ester groups proceeds in two stages, although during the first transesterification stage, some diaryl carbonate can also already be formed. The above Equation 3 further shows a disproportion reaction in which both the dialkyl carbonate and the desired diaryl carbonate are produced from the alkyl aryl carbonate. It is further possible to obtain the alkyl aryl carbonate as the desired reaction product, that is only to operate the first transesterification stage in the first column. Dialkyl carbonates for the process according to the invention are known to those skilled in the art and can be prepared by known processes.

Straight-chain or branched C$_1$–C$_6$-alkyl is, for example, methyl, ethyl, propyl, isopropyl, butyl, isobutyl, pentyl or hexyl.

Straight-chain or branched C$_1$–C$_4$-alkoxy is, for example, methoxy, ethoxy, propoxy, isopropoxy, butoxy or isobutoxy.

Halogen is, for example, fluorine, chlorine or bromine, preferably fluorine or chlorine, particularly preferably chlorine.

The aromatic ester group can be derived from a phenol or from a naphthol, preferably from a phenol and, in the described manner, can be monosubstituted to trisubstituted, preferably monosubstituted or disubstituted, particularly preferably monosubstituted and highly particularly preferably unsubstituted.

Aromatic hydroxyl compounds of the formula (II) which can be used according to the invention are, for example, unsubstituted phenol, o-, m- or p-cresol, o-, m- or p-chlorophenol, o-,m- or p-ethylphenol, o-,m- or p-propylphenol, o-m- or p-methoxyphenol, 2,6-dimethylphenol, 2,4-dimethylphenol, 3,4-dimethylphenol, 1-naphthol and 2-naphthol.

Aromatic hydroxyl compounds which can preferably be used are accordingly, generally those of the formula $$Ar^{11}-OH \qquad (IV),$$

in which

Ar$^{11}$ denotes phenyl or phenyl monosubstituted by C$_1$-C$_4$-alkyl, C$_1$-C$_4$-alkoxy or chlorine.

Among these, unsubstituted phenol is particularly preferred.

Dialkyl carbonates of the formula (III) which can be used according to the invention are, for example, dimethyl carbonate, diethyl carbonate, dipropyl carbonate, dibutyl carbonate and dihexyl carbonate. Dialkyl carbonates which can preferably be used are dimethyl carbonate and diethyl carbonate, particularly preferably dimethyl carbonate.

Diaryl carbonates of the formula (I) which can be prepared according to the invention are, for example, diphenyl carbonate, the isomeric biscresyl carbonates, the isomeric bis(chlorophenyl) carbonates, the isomeric bis(methoxyphenyl) carbonates, the isomeric bis(ethoxyphenyl) carbonates, bis(2,6-dimethylphenyl) carbonate, bis(2,4-dimethylphenyl) carbonate, di-1-naphthyl carbonate and di-2-naphthyl carbonate.

A diaryl carbonate which can be particularly preferably prepared is diphenyl carbonate.

Aralkyl aryl carbonates which occur according to the invention as a partly reacted transesterification product are, for example, C$_1$-C$_6$-alkyl phenyl carbonates, such as methyl phenyl carbonate, ethyl phenyl carbonate, propyl phenyl carbonate, butyl phenyl carbonate and hexyl phenyl carbonate, C$_1$-C$_6$-alkyl (o-, m-, p-cresyl) carbonates, such as methyl (o-cresyl) carbonate, methyl (p-cresyl) carbonate, ethyl (o-cresyl) carbonate, ethyl (p-cresyl) carbonate, C$_1$-C$_6$-alkyl (o-, m-p-chlorophenyl) carbonates, such as methyl (p-chlorophenyl) carbonate or ethyl (p-chlorophenyl) carbonate and analogous compounds. Particularly preferred alkyl aryl carbonates are methyl phenyl carbonate and ethyl phenyl carbonate.

The process according to the invention is described with the aid of the accompanying FIG. 1 and FIG. 2 as follows:

In a column-type reactor (A), the two starting materials, that is a phenol and a dialkyl carbonate which possibly contains small amounts of the corresponding reaction alcohol are conducted in opposite directions to each other over the majority of the reactor section in the sense of a "counter-current transesterification" and are reacted to forth alkyl aryl carbonates and small proportions of diaryl carbonates. The essential characteristics of the technique termed "counter-current transesterification" in the sense of the invention are the following: The starting materials and the resulting products must be conducted in counter-current to each other respectively in pairs, that is the one starting material, here the phenol, is fed in at the upper end of column (1) in the liquid form and the dialkyl carbonate/alcohol mixture is fed in at the bottom end of the column (2) in the gaseous forth, the readily volatile reaction alcohol, together with still unreacted dialkyl carbonate is withdrawn at the head of the column (4) and the poorly volatile alkyl aryl carbonate formed, together with still unreacted phenol, is withdrawn at the foot of the column (8). A liquid phase, which in the present case essentially comprises phenol and the alkyl aryl carbonate formed, and a gas phase, which essentially contains the readily volatile dialkyl carbonate and the reaction alcohol, must be present next to each other, the reaction in the liquid phase starting by dissolution in the liquid phenol of the dialkyl carbonate added in the gaseous stage. The temperatures and pressures must therefore be matched to each other in such a way that no significant evaporation of the liquid phase occurs.

In a second reactor B, the alkyl aryl carbonate produced in the reactor A, is further reacted in the sense of a "reaction distillation". The essential characteristics for a "reaction distillation" in the sense of the invention are the following: The alkyl aryl carbonate intermediate is substantially prevented, by a specially chosen temperature gradient in reactor B, from leaving the reaction part of the reactor at the top or at the bottom. The readily-volatile reaction products, here reaction alcohol and dialkyl carbonate, are withdrawn at the head of column B via (11), and the poorly-volatile reaction product, here the diaryl carbonate, is withdrawn at the foot of the column via (15). The excess phenol can be withdrawn either together with diaryl carbonate end products at the foot of the reactor B at (15) or, preferably, together with the low-boiling products at the head of column B via (11). The conditions in this case are preferably chosen in such a way that a high phenol excess of 2 to 20, preferably of 3 to 15, particularly preferably of 3 to 10 mol per mol of alkyl aryl carbonate is maintained in the reaction zone of the reactor B.

In FIG. 1 and FIG. 2, furthermore, (3) and (9) denote the withdrawal lines for gaseous head product from A and B, which is liquified respectively in condensers (a1) and (b1) and some of which is returned via (5) and (10) as reflux to A and B. (a2) and (a3) are preheaters, (a4) and (b2) are bottom circulation heaters; the bottom outflows from A and B are withdrawn via (6) and (13), partly returned via (7) and (14) to A and B and the remainder conducted as partly reacted transesterification product from A via (8) to B or withdrawn via (15) as crude diaryl carbonate.

The particular technique according to FIG. 2 is described further below; if identical designations are used in FIG. 1 and FIG. 2, they have the same meaning.

By the above described procedure, adapted to the specific transesterification problem, in two column-type reactors connected one after the other, in which various techniques adapted to the particular reaction stage are realised, elevated dialkyl carbonate conversion rates and phenol conversion rates and higher space-time yields are achieved in comparison to the prior art. In particular, in the process according to the invention, significant amounts of the corresponding alcohol can also be. tolerated in the dialkyl carbonate starting material stream, so that not only can pure dialkyl carbonates be used in the process, but also mixtures having smaller amounts of the reaction alcohol, for example from a dimethyl carbonate/methanol separation distillation. In the second reactor, the alkyl aryl carbonate intermediate reacts not only in the sense of a disproportionation according to Equation 3 with itself to form diaryl carbonates and dialkyl carbonates, but additionally to a significant extent with a phenol in the sense of a transesterification reaction according to Equation 2 to form diaryl carbonates and alcohols, as a result of which significantly less dialkyl carbonate is produced as a low-boiling product.

The dialkyl carbonate/alcohol mixture withdrawn at the head of column B is composed of 25 to 98% by weight, preferably 50 to 95% by weight, particularly preferably 75 to 92% by weight, of dialkyl carbonate of the formula (III); the remainder up to 100% by weight is composed of the underlying alcohol $$R^1\text{—OH} \qquad (V),$$

in which $R^1$ has the above meaning.

This dialkyl carbonate/alcohol mixture is itself mixed with excess aromatic hydroxyl compound, the proportion of which depends on the excess of this aromatic hydroxyl compound metered in from column A and the temperature profile applied to the column.

The crude diaryl carbonate withdrawn from the bottom of column B has a purity from 50 to 100% by weight, preferably 80 to 99% by weight, particularly preferably 85 to 98% by weight; the remainder to 100% by weight is composed of alkyl aryl carbonate of the formula $$Ar^1\text{—O—CO—O—}R^1 \qquad (VI),$$

in which $Ar^1$ and $R^1$ have the above meaning.

Phenol (II) used in excess and not completely reacted in column A should be held as far as possible in the central part of B, in order to react with (VI) in the sense of the above Equation 2. If phenol is to be drawn off from B, this is possible in the described manner via the head or via the bottom. Such a phenol to be dragon off then supplements the above described head or bottom discharges from B.

The column A to be used in the first reaction stage of the above described two-stage process and termed a "counter-current column" represents in the simplest case an isothermically heated or, preferably, adiabatically insulated packed tube containing conventional dumped or arranged packings to be used for distillations. At the bottom end, the column can have a stripping section operating at elevated temperatures in which a substantial to complete separation of the fed-in dialkyl carbonate from the liquid phase trickling down is carried out, the dialkyl carbonate being conducted again the vapour phase into the transesterification region of the column. In addition, the column A, at the upper part, can have an enrichment section which separates off co-evaporated phenol or alkyl phenyl carbonate from the low-boiling reaction alcohols or dialkyl carbonates and returns it in the liquid state into the transesterification section of the column. However, the enrichment or stripping section may also be dispensed with.

The dumped packings or arranged packings to be used for the columns A and B are those conventional for distillations, such as are described, for example, in Ullmann's Encyclopädie der Technischen Chemie [Ullmann's Encyclopedia of Industrial Chemistry], 4th edition, volume 2, pp. 528 ff. or in the company leaflets of the relevant apparatus engineering companies. Examples which can be mentioned are: Raschig or Pall rings, Berl, Intalox or Torus saddles, Interpack packings made of various materials, such as glass, ceramics, porcelain, stainless steel, plastic, which, in particular when metal is used, can be processed into a fabric or mesh form. Dumped packings and arranged packings are preferred which have a large surface area, and show good wetting and sufficient residence time of the liquid phase. These are, for example, Pall and Novolax rings, Berl saddles, BX packings, Montz-Pak, Mellapak, Melladur, Kerapak and CY packings.

However, for the columns A and B, not only are packed columns suitable but also those having fixed internals. Tray columns are generally suitable, for example those having sieve trays, bubble-cap trays, valve trays, tunnel trays and centrifugal trays, which can, moreover, be present in various configurations. Among these, those having bubble-cap trays or valve trays having high residence times with good mass transfer, for example bubble-cap tray columns having high overflow weirs, are preferred.

The theoretical plate number of the column to be used as reactor A is 3 to 50, preferably 3 to 30 and particularly preferably 5 to 20 plates, the liquid holdup is 1 to 80%, preferably 10 to 75%, particularly preferably 15 to 70% and very particularly preferably 15–50% of the column internal volume. More precise design of the transesterification section and the stripping section and enrichment section possibly to be used can be made by those skilled in the art.

The column A is operated in such a way that, into the upper half, preferably into the upper third, a phenol stream (1), which can, if required, contain the catalyst in dissolved form, is fed in liquid form, preferably at the temperature prevailing at this position of the column.

The bottom half of column A is charged, preferably above a stripping zone which may be present, via (2) with a dialkyl carbonate stream, generally in vapour form, at temperatures from 120° to 220° C. This dialkyl carbonate stream contains 0 to 5% by weight, preferably 0.1 to 3% by weight and particularly preferably 0.2 to 2% by weight of the corresponding alcohol of the formula (IV). The energy for the evaporation and superheating of the dialkyl carbonate stream can be introduced via a separate, external heat exchanger or a heat exchanger integrated into the column.

After passing through the transesterification zone and possibly after passing through an enrichment zone, the reaction alcohol is withdrawn at the head of the column at (4). It generally still contains excess or unreacted dialkyl carbonate and, when an enrichment section is not present, also certain amounts of the aromatic hydroxyl compound.

After passing the transesterification zone and a stripping section which may be present, a mixture of alkyl aryl carbonate with excess or unreacted phenol, with or without small amounts of diaryl carbonate already formed, with or without soluble catalysts and, in the case of a technique without a stripping section, also with dialkyl carbonate exits at the foot of the column A at (6). The bottom product is preferably fed directly via (8) into the second transesterification column B, but may also previously be concentrated in an appropriate manner, i.e. brought to the desired content of alkyl aryl carbonate, phenol and dialkyl carbonate.

In the context of the transesterification process according to the invention it is expedient to introduce the energy necessary for the reaction in reactor A not only via internal or external heat exchangers of any type, but preferably both with the liquid stream of the aromatic hydroxyl compound and with the dialkyl carbonate fed in the gaseous form. In addition, internal or external heat exchangers can be built into the reactor to compensate for heats of reaction. The column has a more or less high temperature gradient over the entire length.

The catalyst is preferably introduced together with the phenol starting material stream in dissolved or suspended form into the column A via (1). Alternatively, the catalyst can also be added separately, for example in the reaction alcohol or in a suitable inert solvent which is foreign to the system. When heterogeneous catalysts are used, these can be used in a mixture with the packings mentioned in a suitable form instead of packings or as a bed on built-in column trays.

The molar ratio of the starting materials used in the column varies from 0.1–10 mol, preferably from 0.2–5 mol and particularly preferably from 0.5–3 mol of dialkyl carbonate per mol of phenol used.

The first transesterification stage in the reactor A can be carried out at temperatures from 100°–300° C., preferably at temperatures from 120°–250° C. and particularly preferably at temperatures from 150°–240° C. in the column. A temperature gradient to be preferably applied lies in the temperature range given and increases from the column head in the direction of the column foot. In this case, it must be ensured that the reaction temperature in the transesterification region does not lie above the evaporation temperature of the phenol used. It is therefore advantageous to carry out the transesterification according to the invention not only at atmospheric pressure, but alternatively at elevated or reduced pressure from 500 mbar up to 20 bar. A preferred pressure range lies between 0.8 and 15 bar, a particularly preferred pressure range lies between 0.9 and 10 bar.

The space-time loading of the column lies at 0.05–5 g of total amount of reactants per ml of effective column volume per hour, preferably at 0.1–3 g/ml/h, particularly preferably at 0.2–2 g/ml/h; the effective column volume in this case is that of the packing or the volume in which fixed internals are located.

The reactor B (FIGS. 1–2) to be used in the second reaction stage and which is designated a "reaction column" is composed of a column-like tube to which a temperature profile is applied which, increasing from top to bottom, includes a temperature range from 50° to 320° C., preferably 65° to 305° C. and particularly preferably 65° to 250° C. To adjust the temperature gradients in the individual sections of the column-like reactor, these sections can be furnished with insulation or thermostating. The thermostating in this case, according to requirement, can represent heating or cooling. The reactor B can be expanded or constricted in various sections of its overall length, corresponding to the gas loads and liquid loads and the residence times required. For the central part of B, the reaction region, fixed internals are preferred; for the parts in which separations take place, on the other hand, dumped packings and fixed packings are preferred.

At the bottom end of the column B, one or more evaporators, possibly separated by adiabatically insulated column parts, are arranged. These evaporators can be arranged inside or, preferably, outside the column. In an industrial embodiment of the invention, apparatuses conventional in the technology such as circulation evaporators, falling-film evaporators and spiral tube evaporators are used.

Above the evaporator zone, in the central region termed the "reaction zone", fixed internals are preferably used, and particularly preferably those having large liquid holdup, for example bubble-cap trays having high overflow weirs as described in DE 2 503 195. The theoretical plate number in this region is 2 to 50, preferably 2 to 25 and particularly preferably 2 to 15. The liquid holdup in this region is 5 to 80%, preferably 10 to 75%, particularly preferably 15 to 70% and very particularly preferably 5–50% of the internal volume of the internals.

Again, above this region, the column is equipped with other packings or internals which are specially suitable for mass separations by distillation. At the upper end of the column B, an enrichment section is preferably arranged by which a specific reflux to the column can be established.

The column B (FIGS. 1-2) is operated in such a way that above the "reaction zone", a stream, which is taken from the column A at (6) via the line (8), composed of alkyl aryl carbonate and aromatic hydroxyl compound, which can possibly contain small amounts of diaryl carbonate, dialkyl carbonate and a transesterification catalyst, is fed in the liquid state. This stream passes through the "reaction zone" and is there partly converted into diaryl carbonate, and the still unreacted reactants are transported with the aid of the described evaporators in the gaseous state back into the reaction zone and the upper parts of the column B. These condense there and react again to form the diaryl carbonate end product. The diaryl carbonate end product is enriched as the highest boiling reaction component in the bottom region of the column and is there discharged via (15) together with, possibly, homogeneously dissolved catalyst and small amounts of alkyl phenyl carbonate and aromatic hydroxyl compound.

The readily volatile reaction products from the disproportionation reaction according to Equation 3, that is dialkyl carbonates of the formula III, or from the second transesterification stage according to Equation 2, that is the alcohols of the formula (IV), are withdrawn at the head of column B via (11). The phenols which are present in excess or unreacted of the formula (II) can either be discharged at the foot of the column via (15) together with the diaryl carbonate end product of the formula (I) or, in a preferred technique, be discharged together with the low-boiling products at the head of the column B via (11).

In a particular technique (FIG. 2), the crude product mixture (16), which is essentially composed of diaryl carbonate, can be still further reacted and separated in a downstream separate reactor C at pressures from 0.05 to 1.0 bar, pure diaryl carbonate being withdrawn in the sidestream of this column via (15), a diaryl carbonate-containing catalyst bottom product (22) being withdrawn at the foot of the column and the unreacted starting materials and low-boiling products formed being withdrawn via the head at (19). The catalyst bottom product (22) can be returned at a suitable position into the process, for example into the reactor A via (1) or into the reactor B via (8). If partial deactivation takes place, it is, of course, also possible to withdraw a part of the catalyst bottom product and to replace the removed part by a fresh catalyst at a suitable position, for example via (1). The mixture (19) produced as the head product of the column C can be returned at the side into the product stream (8), possibly after equalisation of the pressure, in the transesterification process.

When homogeneously dissolved or suspended catalysts are used, the catalysts which are already active in column A and which are contained in the bottom product (6) are essentially fed into column B and as a result are active in the reactor zone of B. However, there is additionally the possibility, at a position above the reaction zone, to feed in additional catalyst of the same type or a second catalyst into column B. When heterogeneous catalysts are used, these can be used in a mixture with the mentioned packings, in a suitable form instead of packings or preferably as a bed on built-in column trays.

The reaction in column B is carried out at pressure between 50 mbar and 10 bar, preferably between 0.1 and 5 bar and particularly preferably between 0.2 and 2 bar. The temperatures in the region $B_1$ of column B, which is designated the reaction zone, lie between 100° and 300° C., preferably between 120° and 280° C. and particularly preferably between 150° and 260° C.

Catalysts which are useful are heterogeneous and homogeneous catalysts. The heterogeneous catalysts can be arranged as a fixed bed within the column. However, they can also be used in the form of a suspension in the upper to central part of the column, possibly as a mixture with parts of the starting materials, and pass out of the column again at the bottom end together with the poorly volatile reaction products; after being separated off they can be used again. Homogeneous catalysts are likewise used in the upper to central part of the column and can be used here as a mixture with the aromatic hydroxyl compound.

For all reaction steps according to the invention, the same catalysts can be used. These are transesterification catalysts known from the literature for the dialkyl carbonate/phenol transesterification, such as for example hydrides, oxides, hydroxides, alcoholates, amides and other salts of alkali metals and of alkaline earth metals (U.S. Pat. Nos. 3,642,858; 3,803,201; EP 1082), such as of lithium, sodium, potassium, rubidium, caesium, magnesium and calcium, preferably lithium, sodium, potassium, magnesium and calcium and particularly preferably lithium, sodium and potassium. Salts of the alkali metals and of the alkaline earth metals can also be those of organic or inorganic acids, such as of acetic acid, propionic acid, butyric acid, benzoic acid, stearic acid, carbonic acid (carbonates or hydrogencarbonates), phosphoric acid, prussic acid, thiocyanic acid, boric acid, stannic acid, $C_1$–$C_4$-stannonic acids or antimonic acid. Compounds of the alkali metals and of the alkaline earth metals which are useful are preferably the oxides, hydroxides, alcoholates, acetates, propionates, benzoates, carbonates and hydrogencarbonates, particularly preferably hydroxides, alcoholates, acetates, benzoates or carbonates are used.

The alkali metal compounds of alkaline earth metal compounds mentioned are used in amounts of 0.001 to 2% by weight, preferably 0.005 to 0.9% by weight and particularly preferably 0.01 to 0.5% by weight, based on the reaction mixture to be reacted.

Further catalysts which can be used according to the invention are Lewis acid metal compounds such as $AlX_3$, $TiX_3$, $UX_4$, $TiX_4$, $VOX_3$, $VX_5$, $ZnX_2$, $FeX_3$ and $SnX_4$, in which X represents halogen, acetoxy, alkoxy or aryloxy (DE-OS (German Published Specification) 2 528 412, 2 552 907), for example titanium tetrachloride, titanium tetraphenoxide, titanium tetraethoxide, titanium tetraisopropylate, titanium tetradodecylate, tin tetraisooctylate and aluminium triisopropylate, in addition organotin compounds of the general formula $(R^{11})_{4-x}$—Sn(Y)$_x$, in which Y represents a radical $OCOR^{12}$, OH or OR, where $R^{12}$ denotes $C_1$–$C_{12}$-alkyl, $C_6$–$C_{12}$-aryl or $C_7$–$C_{13}$-alkylaryl and $R^{11}$, independently of $R^{12}$, has the meaning of $R^{12}$ and x denotes an integer from 1 to 3, dialkyltin compounds having 1 to 12 C atoms in the alkyl radical or bis-(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid and octylstannonic acid in amounts of 0.001 to 20% by weight (EP 879, EP 880, EP 39 452, DE-OS (German Published Specification) 3 445 555, JP 79/63023), polymeric tin compounds of the formula —[—R,$R^{11}$Sn—O—], for example poly[oxy(dibutylstannylene)], poly[oxy(dioctylstannylene)], poly[oxy(butylphenylstannylene)] and poly[oxy(diphenylstannylene)] (DE-OS (German Published Specification) 3 445 552), polymeric hydroxystannoxanes of the formula —[—RSn(OH)—O—]—, for example poly(ethylhydroxystannoxane), poly(butylhydroxystannoxane), poly(octylhydroxystannoxane), poly(undecylhydroxystannoxane) and poly(dodecylhydroxystannoxanes) in amounts of 0.001 to 20% by weight, preferably of 0.005 to 5% by weight, based on diesters of carbonic acid (DE-OS (German Published Specification) 4 006 520).

Further tin compounds which can be used according to the invention are Sn(II)oxides and have the formula $$X-R_2Sn-O-R_2Sn-Y,$$

in which
X and Y, independently of each other, are to denote OH, SCN, $OR^{11}$ $OCOR^{11}$ or halogen and R is to denote alkyl, aryl (EP 0 338 760).

Further catalysts which can be used according to the invention are lead compounds, with or without triorganophosphines, a chelate compound or an alkali metal halide, for example $Pb(OH)_2.2PbCO_3$, $Pb(O-CO-CH_3)_2$, $Pb(OCO-CH_3)_2.2LiCl$, $Pb(O-CO-CH_3)_2 2PPh_3$ in amounts from 0.001 to 1, preferably from 0.005 to 0.25, mol per mol of carbonate (JP 57/176932, JP 01/093580), other lead(II) compounds and lead(IV) compounds, such as PbO, $PbO_2$, red lead, plumbites and plumbates (JP 01/093560), iron(III) acetate (JP 61/172852), furthermore copper salts and/or metal complexes, for example of alkali metal, zinc, titanium and iron (JP 89/005588), combinations of Lewis acids and protonic acids (DE-OS (German Published Specification) 3 445 553) or element compounds of Sc, Cr, Mo, W, Mn, Au, Ga, In, Bi, Te and lanthanides (EP 338 760).

Furthermore, heterogeneous catalyst systems can be used in the processes according to the invention. Such heterogeneous catalyst systems are, for example, mixed oxides of silicon and titanium, which can be prepared by collective hydrolysis of silicon and titanium halides (JP 54/125617), and titanium dioxides having a high BET surface area >20 m²/g (DE-OS (German Published Specification) 4 036 594).

Catalysts which can preferably be used in the process according to the invention are tin compounds, titanium compounds and zirconium compounds and the above-mentioned alkali metal compounds and alkaline earth metal compounds, particularly preferably usable catalysts are organotin compounds and titanium tetraalkyl esters and titaniumtetraaryl esters.

Some of the amounts of catalysts which are to be used can differ from the amounts mentioned in the literature.

EXAMPLES 1-6

(FIG. 1, reactor A, counter-current transesterification)

The top of a column of 185 cm length and 28 mm diameter which was isothermically thermostatted to 175° C. and packed with V4A stainless steel wire mesh rings (3×3 mm) was charged continuously with a liquid mixture, which was preheated to 160° C., of phenol and the catalyst used in each case. Against this liquid stream was fed gaseous dimethyl carbonate or gaseous mixtures of dimethyl carbonate and methanol, which was (were) vaporised in a separate apparatus and fed in 35 cm above the column foot into the column. At the upper end of the column, which had a short enrichment part (15 cm adiabatic column having a reflux divider) a mixture of methanol and dimethyl carbonate (head product) was continuously drawn off; at the foot of the column a mixture of methyl phenyl carbonate, diphenyl carbonate, a little dimethyl carbonate and the catalyst (bottom product) was continuously dragon off. Since no separate stripping section was present, the dimethyl carbonate could not be completely removed from the bottom product, which led to a dilution of the product concentration in the bottom product. The selectivities with respect to the formation of methyl phenyl carbonate and diphenyl carbonate were >99% for all examples.

In the following Table 1, the initial amounts used, reaction conditions and experimental results are compiled. The results were determined after the establishment of constant conditions by the means over a plurality of measurements.

The top of a 350 cm-long packed column having a 28 mm internal diameter, which was otherwise equipped as described in the Examples 1-6, was charged continuously under the conditions described therein with a mixture of 100 g/h of phenol and 1.4 g/h of octylstannonic acid and, in counter-current, 100 g/h of vaporous dimethyl carbonate. At the upper end of the column, 75 g/h of a mixture of 12.3% by weight of methanol and 87.7% by weight of dimethyl carbonate were continuously withdrawn and at the foot of the column, 125 g/h of a mixture of. 26.8% by weight of methyl phenyl carbonate, 5.4% by weight of diphenyl carbonate, 60.8% by weight of phenol, 7.0% by weight of dimethyl carbonate and the catalyst were continuously withdrawn. This corresponded to a phenol conversion of 26%. The selectivity with respect to the formation of methyl phenyl carbonate and diphenyl carbonate was >99%.

EXAMPLE 8

(FIG. 1, reactor A, counter-current transesterification)

As described in Examples 1-6, a mixture of 150 g/h of phenol and 2.1 g/h of octylstannonic acid was reacted in counter-current with 150 g/h of vaporous diethyl carbonate. At the upper end of the column, after establishment of constant conditions, 115 g/h of a mixture of 6.5% by weight of ethanol and 93.5% by weight of diethyl carbonate were continuously withdrawn and at the foot of the column 185g/h of a mixture of 12.4% by weight of ethyl phenyl carbonate, 0.6% by weight of diphenyl carbonate, 75.0% by weight of phenol, 12.0% by weight of diethyl carbonate and the catalyst were continuously withdrawn. This corresponded to a phenol conversion of 9.1%. The selectivity with respect to the conversion of ethyl phenyl carbonate and diphenyl carbonate was >99%.

EXAMPLES 9-14

(FIG. 1, reactor A, counter-current transesterification)

In contrast to the packed column described in Examples 1-8, a glass bubble-cap tray column having a length of 72 cm and a diameter of 4.75 cm, which was isother-

TABLE 1

| Example No. | Starting materials | | | Bottom product composition | | | | | Space-time yield*) [g/m*h] | Head product | | |
|---|---|---|---|---|---|---|---|---|---|---|---|---|
| | Phenol [g/h] | Catalyst ([g/h]) | DMC/meth DMC content [%] (rate [g/h]) | Rate [g/h] | MPC | DPC | Phenol | DMC | | Rate [g/h] | Methanol [weight %] | DMC [weight %] |
| 1 | 150 | Butylstannonic acid (1.7) | 100 (150) | 180 | 11.7 | 1.1 | 75.0 | 12.2 | 0.022 | 120 | 4.3 | 95.7 |
| 2 | 150 | Octylstannonic acid (2.1) | 100 (150) | 175 | 13.9 | 1.5 | 76.5 | 8.2 | 0.025 | 125 | 4.8 | 95.2 |
| 3 | 250 | Octylstannonic acid (3.5) | 100 (250) | 295 | 10.3 | 1.1 | 78.3 | 10.2 | 0.032 | 209 | 3.5 | 96.5 |
| 4 | 250 | Octylstannonic acid (3.5) | 100 (500) | 292 | 10.8 | 1.1 | 78.8 | 9.4 | 0.033 | 460 | 1.7 | 98.3 |
| 5 | 150 | Octylstannonic acid (2.1) | 98 (150) | 175 | 10.1 | 1.1 | 80.6 | 8.3 | 0.020 | 125 | 5.8 | 94.2 |
| 6 | 150 | Octylstannonic acid (2.1) | 99 (150) | 180 | 11.4 | 1.2 | 78.9 | 8.4 | 0.024 | 120 | 5.4 | 94.6 |

*)Space-time yield for MPC formation and DPC formation calculated as MPC.
DMC = dimethyl carbonate
MPC = methyl phenyl carbonate
DPC = diphenyl carbonate

EXAMPLE 7

(FIG. 1, reactor A, counter-current transesterification)

mically thermostatted to 175° C., having a total of 10 trays and a liquid holdup of 240 ml was used. At the foot of the column was arranged a 35 cm-long feeding piece and at the head of the column was arranged a 40 cm-long enrichment section. The reactions were carried out as in Examples 1-6. The selectivities with respect to methyl phenyl carbonate formation and diphenyl carbonate formation were 99% for all examples.

In Table 2, initial amounts used, reaction conditions and experimental results are compiled. The results were determined, after constant conditions had been established, by taking the means over a number of measurements.

transesterifying to form diphenyl carbonate. The selectivity of the formation of diphenyl carbonate was >99.9%, that is no by-products could be detected.

EXAMPLE 16

(FIG. 1, reactor B, reaction distillation)

In the column apparatus described in Example 15, under the conditions described there, was reacted a mixture of 50 g/h of methyl phenyl carbonate, 200 g/h

TABLE 2

| Example No. | Starting materials | | DMC/meth DMC content [%] (rate [g/h]) | Bottom product composition [weight %] | | | | | Space-time yield*) [g/m*h] | Head product | | |
|---|---|---|---|---|---|---|---|---|---|---|---|---|
| | Phenol [g/h] | Catalyst ([g/h]) | | Rate [g/h] | MPC | DPC | Phenol | DMC | | Rate [g/h] | Methanol [weight %] | DMC [weight %] |
| 9 | 250 | Octylstannonic acid (3.5) | 100 (250) | 280 | 12.5 | 5.1 | 79.7 | 2.6 | 0.055 | 220 | 5.3 | 94.7 |
| 10 | 150 | Octylstannonic acid (2.0) | 100 (150) | 170 | 12.2 | 4.4 | 78.5 | 4.9 | 0.031 | 130 | 5.1 | 94.9 |
| 11 | 250 | Dibutyltin oxide (3.2) | 100 (250) | 275 | 10.7 | 3.0 | 81.4 | 4.8 | 0.041 | 225 | 3.8 | 96.2 |
| 12 | 250 | Titanium (IV) isopropylate (3.7) | 100 (250) | 278 | 10.8 | 3.3 | 80.8 | 4.8 | 0.043 | 225 | 4.0 | 96.0 |
| 13 | 150 | Octylstannonic acid (3.5) | 98 (250) | 273 | 9.2 | 2.5 | 83.7 | 4.6 | 0.035 | 225 | 3.3 | 96.7 |
| 14 | 150 | Octylstannonic acid (3.5) | 99 (250) | 275 | 10.5 | 2.9 | 81.7 | 4.9 | 0.040 | 225 | 3.6 | 96.4 |

*)Space-time yield for MPC formation and DPC formation calculated as MPC.
DMC = dimethyl carbonate
MPC = methyl phenyl carbonate
DPC = diphenyl carbonate

EXAMPLE 15

(FIG. 1, reactor B, reaction distillation)

A column-type reactor was used, which was built up, viewed from top to bottom, in the following way:

a dephlegmator heated to 95° C., 20 cm in length, having an attached simple distillation device and low-boiler draw-point;

starting material feeding point;

10-tray sieve-plate column, isothermically thermostatted statted to 185° C., of length 65 cm and internal diameter 4.5 cm;

tube (evaporator 2) isothermically thermostatted to 270° C., of length 25 cm and internal diameter 2.8 cm, packed with V4A stainless steel wire mesh rings (3×3 mm);

adiabatically insulated column of length 25 cm and internal diameter 2.8 cm, packed with stainless steel V4A wire mesh rings;

spiral tube evaporator (evaporator 1), isothermically thermostatted to 265° C., of length 25 cm having a bottom product draw-off point.

A mixture of 75 g/h of methyl phenyl carbonate, 175 g/h of phenol and 3 g/h of octylstannonic acid was continuously fed into this reactor at the feeding point above the sieve-point column. At the same time, a gentle nitrogen stream of 2 [1.h$^{-1}$] from the spiral tube evaporator was passed in the opposite direction to this starting material stream. After establishment of constant conditions, at the head of the apparatus, 195 g/h of a mixture of 2.2% by weight of methanol, 13.7% by weight of dimethyl carbonate and 84.1% by weight of phenol were continuously withdrawn, and at the foot of the column, 61 g/h of a mixture of 1.5% by weight of phenol, 0.9% by weight of methyl phenyl carbonate and 97.6% by weight of diphenyl carbonate were continuously withdrawn. This represented a space-time yield for the formation of diphenyl carbonate of 0.06 g/mlh, based on the reactor volume. 18.6% of the methyl phenyl carbonate used reacted with phenol, of phenol and 3.25 g/h of octylstannonic acid. After establishment of constant conditions, at the head of the apparatus, 210 g/h of a mixture of 1.0% by weight of methanol, 5.4% by weight of dimethyl carbonate and 93.6% by weight of phenol were continuously withdrawal and, at the foot of the column, 48 g/h of a mixture of 9.4% by weight of phenol, 1.9% by weight of methyl phenyl carbonate and 88.7% by weight of diphenyl carbonate were continuously withdrawn. This represented a space-time yield for the formation of diphenyl carbonate of 0.048 g·ml$^{-1}$·h$^{-1}$, based on the reactor volume. 20.5% of the methyl phenyl carbonate used reacted with phenol, transesterifying to form diphenyl carbonate. The selectivity of the formation of diphenyl carbonate was >99.9%, that is no by-products could be detected.

EXAMPLE 17

(Reactor B, reaction distillation)

In a column apparatus as described in Example 15, in which, instead of the 10-tray sieve-plate column, a 10-tray bubble-cap tray column, isothermically thermostatted to 183° C., of length 72 cm and internal diameter 4.75 cm was used, there was reacted, under the conditions described there, a mixture of 150 g/h of methyl phenyl carbonate, 350 g/h of phenol and 6.25 g/h of octylstannonic acid. After establishment of constant conditions, at the head of the apparatus, 365 g/h of a mixture of 1.3% by weight of methanol, 8.5% by weight of dimethyl carbonate and 90.2% by weight of phenol was continuously withdrawn and, at the foot of the column, 135 g/h of a mixture of 6.2% by weight of phenol, 14.0% by weight of methyl phenyl carbonate and 79.8% by weight of diphenyl carbonate were continuously withdrawn. This represents a space-time yield for the formation of diphenyl carbonate of 0.085 g·ml$^{-1}$·h$^{-1}$, based on the reactor volume. 16.6% of the methyl phenyl carbonate used reacted with phenol with transesterification to form diphenyl carbonate. The selectivity of the formation of diphenyl carbonate was >99%, that is no by-products could be detected.

It can be seen from the examples that by means of the technique according to the invention, which is adapted to the specific transesterification problem, in the first transesterification stage according to Equation 1, even at relatively low temperatures without application of pressure and large excesses of dialkyl carbonate, considerably greater space-time yields of aryl carbonate formation and alcohol formation of 0.02 to 0.06 g/mlh are achieved, in comparison to the prior art (<0.02 g/mlh), where, at the same time, very high selectivities >99.9% can be achieved, that is no by-products >0.1% by weight could be detected in the product streams. The conversion of the alkyl aryl carbonates proceeds by the technique according to the invention almost quantitatively in a reaction distillation apparatus, where these are converted not only by a disproportionation reaction according to Equation 3, but also, to a considerable extent, by transesterification with phenol to give the diaryl carbonate.

What is claimed is:

1. A process for the preparation of a diaryl carbonate of the formula $$Ar^1-O-CO-O-Ar^1$$

in which
Ar$^1$ denotes unsubstituted phenyl or naphthyl or mono-substituted to trisubstituted phenyl, the substituents being identical or different and belonging to the group comprising C$_1$–C$_4$-alkyl, C$_1$–C$_4$-alkoxy and halogen,
by transesterification of 1 mol of an aromatic hydroxyl compound of the formula $$Ar^1-OH$$

in which Ar$^1$ has the meaning mentioned, with 0.1 to 10 mol of a dialkyl carbonate of the formula $$R^1-O-CO-O-R^1$$

in which
R$^1$ denotes straight-chain or branched C$_1$–C$_6$-alkyl, cyclopentyl or cyclohexyl,
in the presence of a transesterification catalyst known per se in column apparatuses known from transesterifications, wherein the transesterification reaction is carried out in two columns connected one after the other in such a way that
a) in the first column, the aromatic hydroxyl compound is conducted in the liquid state from head to bottom and the dialkyl carbonate is conducted in the gaseous state against this liquid stream, the temperature being kept in the range from 100° to 300° C. and the pressure being kept in the range from 0.5 to 20 bar, and the dialkyl carbonate containing a portion from 0 to 5% by weight of the underlying alcohol, based on the overall weight of dialkyl carbonate and alcohol, that
b) at the head of the first column, the alcohol underlying the dialkyl carbonate and liberated in the transesterification is withdrawn in the gaseous state and at the bottom of the first column, a partly reacted transesterification product essentially composed of alkyl aryl carbonate is withdrawn in the liquid state, that c) the bottom stream of the first column is fed into the central part of a second column, the temperature of which is kept in the range from 60° to 320° C. and the pressure of which is kept in the range from 0.05 to 10 bar, depending on the boiling point of the bottom stream fed in from the first column, a temperature gradient being applied to this second column in such a way that the alkyl aryl carbonate contained in the bottom stream fed in can escape from the central part of the second column essentially neither to the head nor to the bottom and that d) at the head of the second column, a mixture of dialkyl carbonate, the underlying alcohol and excess aromatic hydroxyl compound and at the bottom of the second column, diaryl carbonate, which can contain alkyl aryl carbonate and aromatic hydroxyl compound, are withdrawn.

2. The process of claim 1, wherein aromatic hydroxyl compounds of the formula $$Ar^{11}-OH,$$

are used, in which
Ar$^{11}$ denotes phenyl or phenyl monosubstituted by C$_1$–C$_4$-alkyl, C$_1$–C$_4$-alkoxy or chlorine.

3. The process of claim 2, wherein unsubstituted phenol is used.

4. The process of claim 1, wherein dimethyl carbonate or diethyl carbonate is used as the dialkyl carbonate.

5. The process of claim 4, wherein dimethyl carbonate is used.

6. The process of claim 1, wherein in the process section according to c), in the central part of the second column, a phenol excess of 2 to 20 mol per mol of alkyl aryl carbonate is established.

7. The process of claim 1, wherein the first column is equipped with packings or internals, has a theoretical plate number from 3 to 50 and its liquid holdup is 1 to 80% of the column internal volume.

8. The process of claim 7, wherein the liquid holdup of the first column is 10–75% of the column internal volume.

9. The process of claim 8, wherein the liquid holdup of the first column is 15–70% of the column internal volume.

10. The process of claim 9, wherein the liquid holdup of the first column is 15–50% of the column internal volume.

11. The process of claim 1, wherein the second column is equipped with packings or internals.

12. The process of claim 11, wherein the second column is equipped in the central part with internals and is equipped with packings in the part below and the part above.

13. The process of claim 11, wherein the central part of the second column which is equipped with internals has a theoretical plate number from 2 to 50 and a liquid holdup from 5 to 80% of the internal volume of the internals.

14. The process of claim 13, wherein the central part of the second column has a theoretical plate number from 2 to 25.

15. The process of claim 14, wherein the central part of the second column has a theoretical plate number from 2 to 15.

16. The process of claim 13, wherein the central part of the second column has a liquid holdup from 10 to 75% of the internal volume of the internals.

17. The process of claim 16, wherein the central part of the second column has a liquid holdup from 15 to 70% of the internal volume of the internals.

18. The process of claim 1, wherein a further distillation column for isolation of the diaryl carbonate is connected downstream of the bottom of the second column.

19. The process of claim 1, wherein 1 mol of the aromatic hydroxyl compound is transesterified with 0.2 to 5 mol of the dialkyl carbonate.

20. The process of claim 19, wherein 1 mol of the aromatic hydroxyl compound is transesterified with 0.5 to 3 mol of the dialkyl carbonate.

* * * * *